United States Patent [19]

Burton

[11] 4,205,665

[45] Jun. 3, 1980

[54] GRAVITY LUMBAR REDUCTION METHOD

[76] Inventor: Charles V. Burton, 18409 Minnetonka Blvd., Wayzata, Minn. 55391

[21] Appl. No.: 859,175

[22] Filed: Dec. 9, 1977

Related U.S. Application Data

[63] Continuation of Ser. No. 683,248, May 5, 1976, abandoned.

[51] Int. Cl.[2] .................... A61F 5/00

[52] U.S. Cl. .................... 128/68; 128/75

[58] Field of Search .................... 128/74, 75, 78, 71, 128/68, 69

[56] References Cited

U.S. PATENT DOCUMENTS

| | | | |
|---|---|---|---|
| 309,678 | 12/1884 | Aubin | 128/71 |
| 1,116,773 | 11/1914 | West et al. | 128/75 |
| 2,287,863 | 6/1942 | Buckley | 33/379 X |
| 2,546,425 | 3/1951 | Broeker | 254/122 |
| 2,774,349 | 12/1956 | Judovich | 128/71 |
| 3,589,358 | 6/1971 | Megal | 128/71 |
| 3,685,511 | 8/1972 | Alavarez | 128/71 X |
| 3,786,803 | 1/1974 | Petulla et al. | 128/75 |
| 3,806,109 | 4/1974 | Weber et al. | 269/323 |

FOREIGN PATENT DOCUMENTS

| | | | |
|---|---|---|---|
| 318322 | 2/1957 | Switzerland | 128/71 |
| 883964 | 12/1961 | United Kingdom | 128/71 |

*Primary Examiner*—Robert W. Michell
*Assistant Examiner*—Michael H. Thaler
*Attorney, Agent, or Firm*—Merchant, Gould, Smith, Edell, Welter & Schmidt

[57] ABSTRACT

A method and apparatus for supporting a patient by the upper body below the neck and above the lumbar spine on an inclined member for lumbar reduction therapy under the force of gravity. The inclined member preferably has an adjustable angle of tilt. The patient is supported at an angle and for a period of time commensurate with his ability to tolerate stress.

2 Claims, 6 Drawing Figures

GRAVITY LUMBAR REDUCTION METHOD

This is a continuation of application Ser. No. 683,248, filed May 5, 1976, now abandoned.

BACKGROUND OF THE INVENTION

Back and leg pains are known as common complaints in medicine. According to National Institutes of Health figures, approximately seven million people were under a physician's care for low back pain in the United States in 1971. Early in this century, mechanical back pain syndromes involving the sacro-iliac and lumbar facet joints were well documented. It was then believed that all back and leg pain was due to mechanical factors. Not until 1934 was the degenerative etiology of intervertebral lumbar disc herniation and its relation to back and sciatic pain accurately recognized.

When a herniated disc produces significant neurologic deficit by compression of an anterior primary nerve root, physicians consider surgical decompression the proper treatment. The great majority of degenerative disc cases, however, are less serious and more conservative treatment is indicated prior to the consideration of surgical intervention.

It has been observed that most patients with protruded lumbar discs and insignificant neurologic deficit can be effectively cured by two to three months of complete bed rest. Major problems of instituting such therapy include the social and economic impact of incapacitating a wage earner or active household head for such a long period of time. It appears that many discectomies may be performed for the purpose of expediency alone to avoid such prolonged incapacitation. The therapy and apparatus of this invention achieves the desired beneficial result without surgery or extended periods of incapacitation.

When back surgery is performed, failure rates are variously estimated as being between 10% and 40%. Painful "failed back surgery syndrome" due to scarring adhesions of the arachnoid and nerve fibers of the cauda equina in the lumbo-sacral area is common. There is thus a need for more effective means of short term, conservative therapy for patients with lumbar degenerative disc disease associated with disc protrusion for whom surgery is not immediately indicated, and for those suffering from failed back surgery syndrome who can be helped by stretching or loosening scar tissue, which need is met by the apparatus and method of this invention.

Known traction methods such as Buck's and pelvic traction, have traditionally been used in an effort to achieve distraction or reduction of the lumbar spine. It has recently been shown by Dr. A. Nachemson, in "The Load On Lumbar Disc In Different Positions Of The Body", *Clinical Orthop,* 45: 107-122, that even in the relaxed supine position, there is loading of a normal lumbar disc. In moderately degenerated discs the vertical load on the annulus fibrosus is higher than normal. It is unlikely that conventional known traction can achieve true lumbar reduction by producing negative pressure on the disc interspaces.

Various stretching techniques have also been tried over the years with limited success because the human body is better able to tolerate and compensate for stress applied gradually over a period of time, than the sudden application of high forces.

Negative loading of the lumbar spine may be achieved by supporting the upper body above the lumbar spine as by the chest, sides or under the arms and allowing the lower body to hang under the force of gravity. A device for supporting the upper body while the lower body depends in a vertical position at 90° to the horizontal is disclosed in U.S. Pat. No. 3,353,532 issued to L. C. Ellison on Nov. 21, 1967.

The inventor of the present apparatus and method supervised construction of apparatus, in 1971, to support a patient with a protruded lumbar disc in a vertical, non-inclined or fully dependent position by a chest harness. The device was utilized during the day for ten days following which the patient became asymptomatic. However, hanging in a fully dependent position is acceptable only to a few strong patients. Depending on the construction of the supporting means, unnatural loads may be applied to the chest, sides or shoulders, which stresses are particularly hard on an already weakened patient. For a patient suffering from failed back surgery syndrome, such hanging can result in such a dramatic increase in pain that it may be impossible for the patient to tolerate.

SUMMARY OF THE INVENTION

Accordingly, the present invention comprises a method and apparatus for lumbar reduction thereapy utilizing the force of gravity. A patient is supported by the upper body below the neck and above the lumbar spine on an inclined member. The angle of tilt of the inclined member is preferably adjustable. Lumbar reduction is thereby achieved without the sudden application of unnatural stress. The time during which the patient is supported in such a fashion is important for successful results. It is considered preferable for the patient to remain supported continuously for as long as he is able to tolerate the stress. The longer a patient remains supported, the more effective the therapy. An angle of, for example, approximately 30 degrees to the horizontal is sufficient to produce significantly useful negative loading on the lumbar spine.

The method particularly includes gradually increasing the angle of tilt to the totally dependent, or 90°, position, if possible, thereby progressively increasing the tractive force in a more tolerable fashion. The angle is increased according to patient tolerance of discomfort due to the apparatus used and pain due to his condition. According to this method, the patient would be supported at a reduced angle of up to 30° or more for a significant time of several hours or longer. The angle would be increased by an increment of, for example, 10° upon patient toleration of the smaller angle. It might take days or weeks for a patient to progress in this incremental way to a fully dependent position. Some patients may never reach the fully dependent position due to an inability to accept the stress. The angle the patient eventually reaches is less important than the total time in therapy.

The primary support may comprise means for supporting the upper body, and may partially or completely enclose the thorax. The inclined surface provides a secondary support for the patient at angles less than 90° and conveniently may comprise an adjustable bed. The primary support may be attached to the bed or bed frame as by an overhead support.

BRIEF DESCRIPTION OF THE DRAWINGS

A preferred embodiment of the apparatus for carrying out the method has been chosen for purposes of illustration and description wherein.

THE PREFERRED EMBODIMENT

Figure 1:
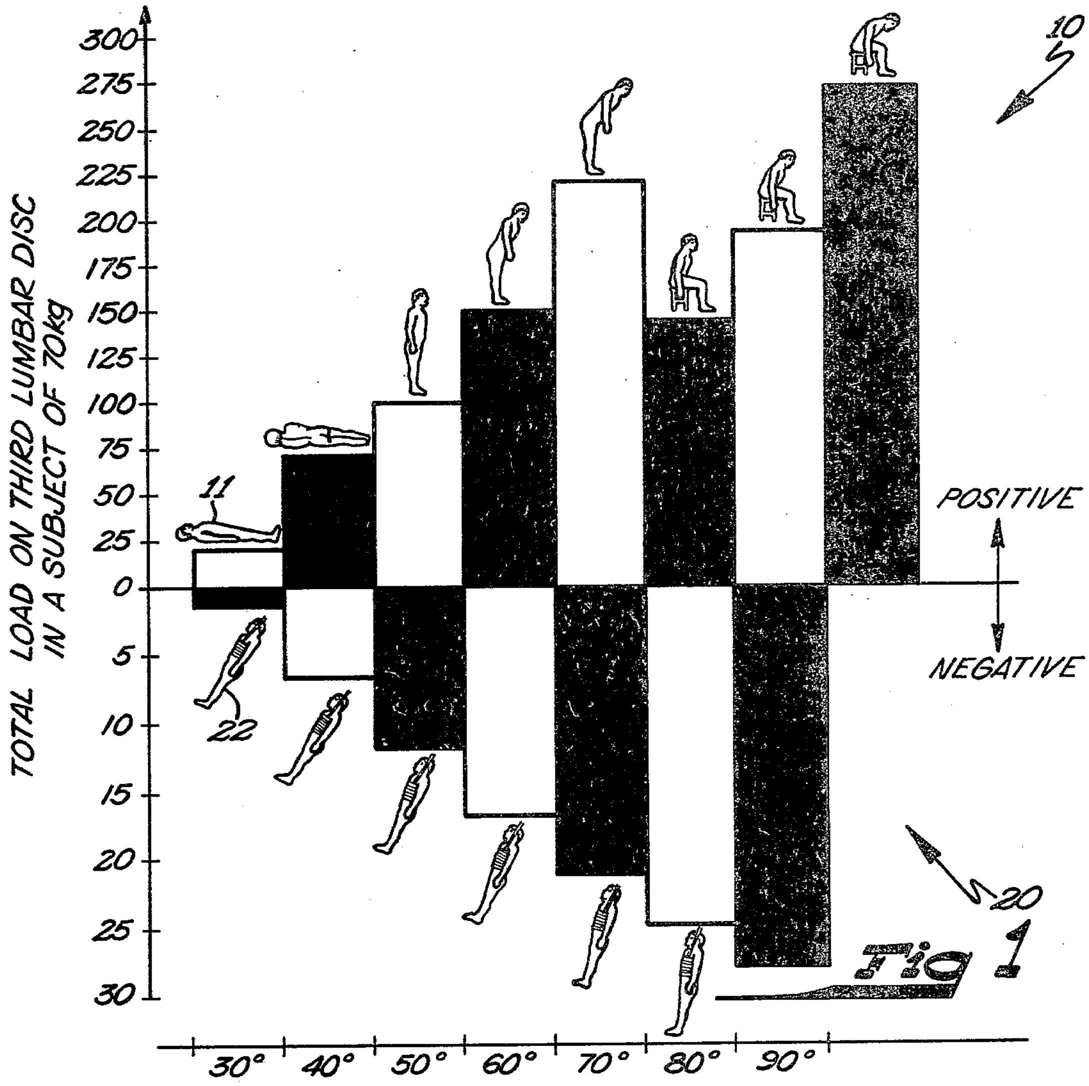
FIG. 1 is a chart illustrating positive and negative lumbar loading for various body positions.

It has been shown by Dr. A. Nachemson that there is a positive load on each lumbar disc which varies with the position assumed by a subject. Referring to FIG. 1, a graph 10 illustrates the load on the third lumbar disc in a subject of 70 kilograms of average build in various positions of reclining, standing and sitting. It is important to note that even in the fully relaxed supine position 11 there is a load of nearly 25 kg. on the third lumbar disc. It is difficult for conventional Buck's or pelvic traction applied to a reclining patient to achieve true lumbar reduction by creation of a negative loading force on the disc interfaces. Patients suffering from a protruded lumbar disc, failed back surgery syndrome, or other lumbar degenerative disc problems, require very long periods of bed rest or traction in the reclining position for successful help. Conventional traction often does little more than keep a patient in bed.

High tractive forces can cause great pain to an individual with an already painful back problem. It is particularly difficult to apply traction to a patient who has had several unsuccessful surgical operations due to the incapacitating pain they already suffer.

The present invention contemplates applying adjustable gravitational force for lumbar reduction therapy. The gravitational force is adjusted by supporting the patient primarily by the upper body above the lumbar spine on an incline or tilt. The force of gravity on the lower body produces distraction of the lumbar spine. By adjusting the angle of tilt the force can be adjusted to a tolerable level for the patient. As improvement of the patient's condition occurs and, as the patient's tolerance of the hanging position increases, the angle of tilt may be increased to increase the force. The angle may be increased in increments. The patient may spend a significant period of time at a given angle, generally one or several hours or longer, but in any case not more than is commensurate with the patient's ability to withstand the physical stress.

The lower graph 20 of FIG. 1 shows the resultant distractive load in a subject at various angles of tilt. At 30° (22) a small negative load is created, A small load will exist at smaller angles. Each 10° increase results in a significant increase in load on the lumbar disc. At 90° the entire weight of the lower body below the disc acts as a negative load. It will be appreciated that even a small load, if continually applied, can be significant over a long time period.

The preferred course of treatment according to the present method involves initially applying a small load at a small angle of tilt continually to the patient for a significant period of time. The angle is progressively increased as tolerable. According to one method the patient may determine when to increase the load and by how much. The temporal element is considered more important than the size of the load. Some patients may never achieve the fully dependent or 90° position. By way of example, it is anticipated that previously unoperated patients with a protruded disc will be maintained by this method for 10 to 14 days following which it will be discontinued. Patients with failed surgery may be treated for 3 to 4 weeks in the hospital and maintain a minimum schedule for one hour twice a day thereafter.

Certain problems may be associated with treatment under this method. Postural hypotension could occur in the unacclimated patient, but may be treated by the use of mild vasopressers. Dependent edema is avoided by the use of thigh length support stockings.

Figure 2:
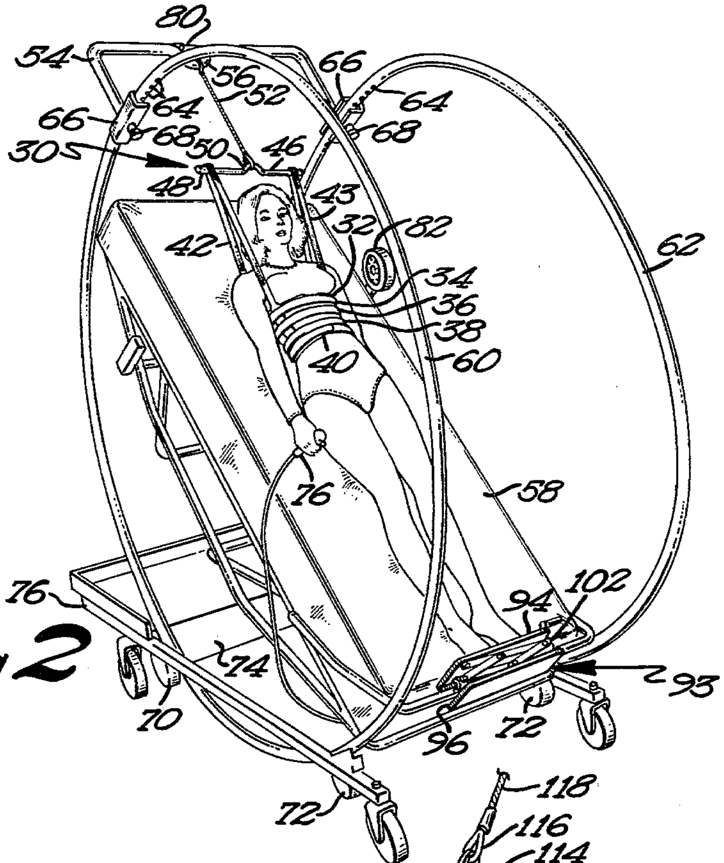
FIG. 2 is a perspective view of an embodiment of the invention apparatus.

A preferred apparatus for practicing the aforedescribed method is shown in FIG. 2. A support device 30 supports a patient by the upper body. In the embodiment shown, a chest harness 32 is wrapped about the thorax of the patient. It is composed of a plurality of coupling means such as belts 34, 36, 38 which couple about or enclose the thorax. The lower belt 38 encloses the patient just under the rib cage and the remainder of the belts in conjunction with a vest 40 enclose and grip the rib cage. The vest may be constructed of heavy material or a net or mesh of strong fiber like nylon. The mesh may be constructed in such a manner as to grip the chest when pulled in a vertical direction along the patient's body. The belts are made of strong fabric and attached in any suitable known way to the vest as by sewing. Right and left vertical straps 42, 43 are attached to vest 40 and belts 34, 36, 38 at the right front and rear and left front and rear of the harness, respectively. Straps 42, 43 are preferably of one piece construction. Harness 32 is more particularly described in copending application Ser. No. 683,276 of Charles V. Burton and Walter Lossing filed on May 5, 1976. Other types of harness capable of properly supporting the entire weight of a patient by the upper body could be used.

Straps 42, 43 of harness 32 loop over opposite ends of spreader 46. A pair of small detents 48 are located at either end of spreader 46 to properly position and retain straps 42, 43. There is a U-shaped bend 50 in the center of spreader 46 to receive a loop at one end of support cable 52 the other end of which also has a loop to receive a U-shaped bend 56 in traction bar 54. As may be appreciated bends 50 and 56 serve to center the harness 32 and patient in the apparatus.

The adjustable incline preferably comprises a bed which forms a secondary support surface upon which the patient partially rests at angles less than 90°. The bed 58 is mounted between two circular hoops 60, 62 which are fixed to the bed frame at or near the corners. Each hoop 60, 62 has several holes as at 64 located in it near the head of bed 58. Located on the ends of traction bar 54 are channels 66 which include spring loaded pins 68 to detachably connect to hoops 60, 62. Pins 68 register in holes 64 to locate bar 54 in a suitable position to properly support the patient and to move with bed 58. Traction bar 54 could be attached to the frame of bed 58 by other means such as by members connected to the bed frame. It will be readily understood that however the angle of incline of bed 58 changes, the patient will always be supported from overhead.

Hoops 60, 62 rest on rollers 70, 72 rotatably mounted to cradle 76. Rollers 70 (one not shown) are driven by drive motor 74. Motor control 76 may be used to control the drive motor to rotate the bed to any angle. The friction between rollers 70 and hoops 60, 62 is sufficient to thereby rotate bed 58 to any angle of tilt. Such motor driven beds are known in the medical field.

Figure 3:
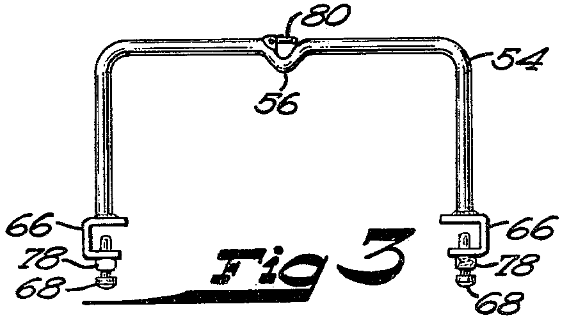
FIG. 3 shows a traction bar of the apparatus of FIG. 2 in detail.

The construction of traction bar 54 may be more readily appreciated by reference to FIG. 3. Channels 66 are shaped with openings sufficiently large to receive hoops 60, 62. The distance between the two channels must be sufficient, as will be appreciated, to fit over hoops 60, 62 so that traction bar 54 may be installed on the bed. The bar may be installed first by locating one channel over its repective hoop, moving the channel so that the hoop is fully located in the channel while pin 68 is retracted and then locating the other channel over the other hoop. Springs 78 are expansion springs and serve to bias pins 68 in an upward direction. After both channels have been located over their respective hoops pins 68 may be inserted into their respective holes 64. A spring loaded snap lock 80 located across bend 56 presents the loop in cable 52 from shifting off center.

Figure 4:
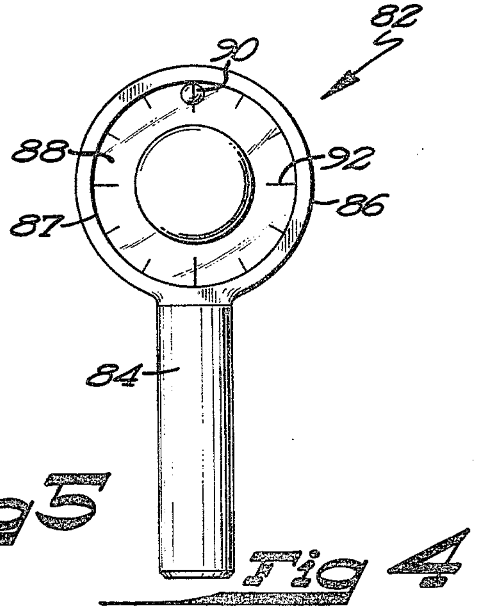
FIG. 4 shows an angle indicator of the apparatus of FIG. 2 in detail.

An angle indicator 82 is attached to the frame of bed 58 (FIG. 2) so that the patient may see what the angle of tilt is. As more particularly shown in FIG. 4, angle indicator 82 has a shaft 84 which may be attached to the bed frame by bolts, clamps or any suitable means, and a head 86. The head is filled with viscous liquid 88 under a transparent face 87 which has markings 92 every 10° or so. The angle of tilt is indicated by the presence of a bubble 90 adjacent markings 92. Indicator 82 may be constructed in a conventional manner for bubble indicators.

Figure 5:
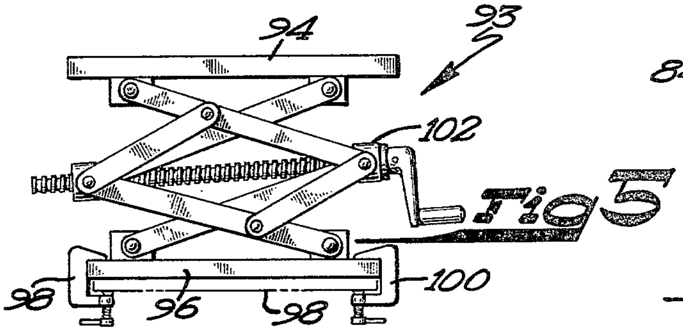
FIG. 5 shows a foot stop of the apparatus of FIG. 2 in detail.

An adjustable foot stop 93 is located at the foot of bed 58. As seen in FIG. 5, foot stop 93 is constructed of an upper platform 94 and a lower platform 96 which is clamped to the existing bed foot board 98 by clamps 100. A crank operated scissors mechanism 102 may be operated to adjust the position of upper platform 94 to just below the patient's feet as a safety device to help protect the patient from a fall if one of the primary support elements fails.

Figure 6:
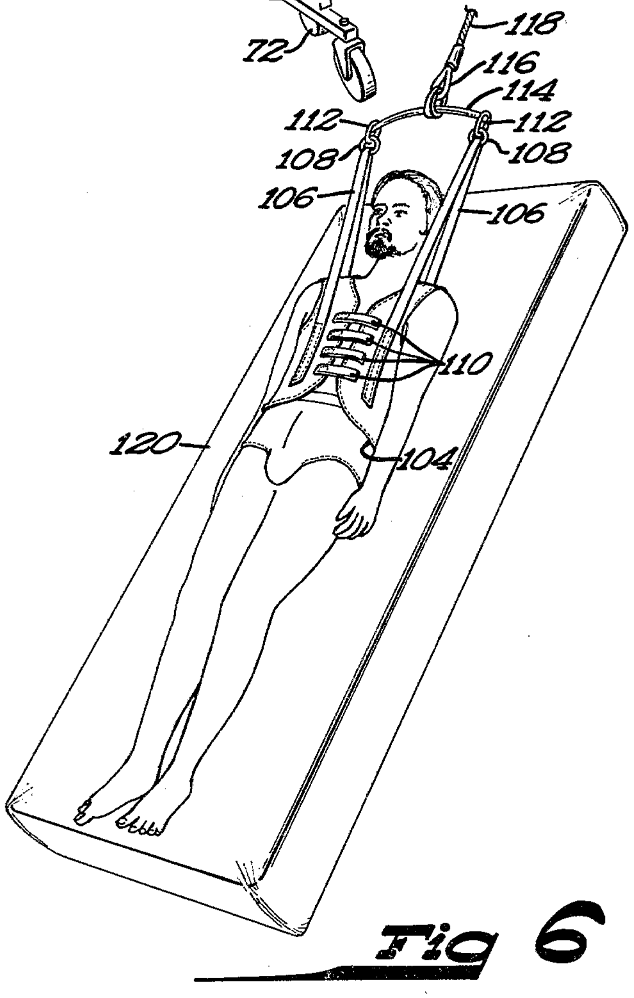
FIG. 6 shows an alternative embodiment using a tilt board.

An alternative embodiment is shown in FIG. 6. A vest 104 of heavy canvas of other suitable material is worn by the patient. Straps 106 are sewn or otherwise attached to the vest front and back. The straps pass through loops 108 which may be either welded or loosely fitted to end tabs 112 of stretcher 114. A center tab 116 receives a loop on one end of cable 118. The vest is tightly closed by means of tabs 110 sewn to one side and attachable to the other side by a strong fastener. The patient is disposed on an inclined member 120 which may be a pad, box spring, or simple tilt board. The inclined member 120 may be supported at any angle by simple supports such as saw horses, or by a more permanent frame structure. Cable 118 may be supported at the end not shown by a hook on a door or by a frame member constructed in conjunction with a frame for supporting member 120.

The contemplated scope of the method of therapy and of the traction apparatus of the present invention may be more readily understood by reference to the appended claims.

What is claimed is:

1. A method of gravity lumbar reduction therapy, which comprises the steps of:

(a) disposing the body of a patient on a support member that is inclined at an angle with regard to the horizontal;

(b) suspending the patient by the rib cage in a head-up orientation with the patient's feet being unsupported, wherein the patient is suspended from substantially directly above the patient's shoulders regardless of the angle of the support member to produce an axial elongation of the spine, wherein the suspending step comprises:

(i) firmly and frictionally grasping the rib cage of the patient below the patient's arm pits and at least partially underneath the rib cage; and (ii) hanging the patient by the rib cage with the weight of the patient's body being supported at the rib cage;

(c) maintaining the patient in the disposed and suspended position to allow the force of gravity to act on the unsupported lower body, whereby a non-injurious stretching of the lumbar spine is achieved; and (d) progressively increasing the angle of the support member to a maximum angle in accordance with the patient's ability to tolerate the stress imposed on the patient's spine and maintaining the patient in the disposed and suspended position at each increased angle of the support member, and wherein the maximum angle includes 90° relative to the horizontal in appropriate cases.

2. A method according to claim 1, including the step of supporting the patient at each increased angle of the support member for a significant period of time.

* * * * *

UNITED STATES PATENT AND TRADEMARK OFFICE

CERTIFICATE OF CORRECTION

PATENT NO. : 4,205,665

DATED : June 3, 1980

INVENTOR(S) : Charles V. Burton

It is certified that error appears in the above-identified patent and that said Letters Patent are hereby corrected as shown below:

On the face of the patent, please insert the following information regarding the Assignee of this patent:

--Assignee: Abbott-Northwestern Hospital, Inc., Minneapolis, Minnesota--.

Column 1, line 12, "1971" should read -- 1972 --.

Signed and Sealed this

*Ninth* Day of *December 1980*

[SEAL]

*Attest:*

SIDNEY A. DIAMOND

*Attesting Officer* *Commissioner of Patents and Trademarks*